(12) United States Patent
Lim

(10) Patent No.: US 7,799,055 B2
(45) Date of Patent: Sep. 21, 2010

(54) MINIMAL SPACING SPINAL STABILIZATION DEVICE AND METHOD

(75) Inventor: Roy Lim, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 410 days.

(21) Appl. No.: 11/483,049

(22) Filed: Jul. 7, 2006

(65) Prior Publication Data

US 2008/0021458 A1 Jan. 24, 2008

(51) Int. Cl.
- *A61B 17/58* (2006.01)
- *A61B 17/70* (2006.01)
- *A61B 17/76* (2006.01)
- *A61B 17/84* (2006.01)

(52) U.S. Cl. .................. 606/246; 606/60; 606/257; 606/261; 606/270; 606/279; 606/914

(58) Field of Classification Search ............ 606/60, 606/246–279, 914
See application file for complete search history.

(56) References Cited

U.S. PATENT DOCUMENTS

| | | | |
|---|---|---|---|
| 4,887,595 A * | 12/1989 | Heinig et al. | ............... 606/254 |
| 5,129,899 A | 7/1992 | Small et al. | |
| 5,728,127 A | 3/1998 | Asher et al. | |
| 5,800,433 A | 9/1998 | Benzel et al. | |
| 6,022,350 A | 2/2000 | Ganem | |
| 6,267,765 B1 | 7/2001 | Taylor et al. | |
| 6,290,703 B1 * | 9/2001 | Ganem | ............... 606/250 |
| 6,315,779 B1 | 11/2001 | Morrison et al. | |
| 6,648,885 B1 * | 11/2003 | Friesem | ............... 606/278 |
| 2001/0037111 A1 | 11/2001 | Dixon et al. | |
| 2003/0045875 A1 | 3/2003 | Bertranou et al. | |
| 2003/0171749 A1 | 9/2003 | Le Couedic et al. | |
| 2003/0187435 A1 * | 10/2003 | Lin | ............... 606/61 |
| 2004/0006342 A1 | 1/2004 | Altarac et al. | |
| 2004/0243126 A1 | 12/2004 | Carbone et al. | |
| 2005/0131406 A1 * | 6/2005 | Reiley et al. | ............... 606/61 |
| 2005/0131409 A1 | 6/2005 | Chervitz et al. | |
| 2006/0217719 A1 * | 9/2006 | Albert et al. | ............... 606/61 |
| 2006/0229608 A1 * | 10/2006 | Foster et al. | ............... 606/61 |

FOREIGN PATENT DOCUMENTS

| | | |
|---|---|---|
| FR | 2 785 787 | 5/2000 |
| WO | WO 99/52462 | 10/1999 |
| WO | WO 2006/101737 | 9/2006 |

* cited by examiner

*Primary Examiner*—Thomas C Barrett
*Assistant Examiner*—Sameh Boles

(57) ABSTRACT

Stabilization systems for stabilizing one or more vertebral levels are provided. The systems include anchors engageable to the vertebrae and at least one connecting member that includes a window to receive the anchors and mounting portions extending from opposite ends of the connecting member into the window for engagement with the anchors. The connecting member can flex in response to spinal loading to provide dynamic stabilization, although rigid engagement relationships are also contemplated.

26 Claims, 5 Drawing Sheets

MINIMAL SPACING SPINAL STABILIZATION DEVICE AND METHOD

BACKGROUND

Various types of devices and systems have been used to stabilize portions of bones including the spine. Spinal stabilization techniques have employed plating and connecting members on the posterior, anterior, lateral, postero-lateral and antero-lateral portions of a spinal column segment. Such systems can provide rigid or dynamic fixation of a spinal column segment for the repair of injured or diseased vertebrae, intervertebral discs, and other elements of the spinal column. There remains a need for dynamic stabilization systems that are adaptable for various stabilization requirements in a spinal procedure.

SUMMARY

Spinal stabilization systems are provided that include connecting member systems positionable between at least two anchors. The connecting member systems can couple the anchors to one another, even if the spacing between the anchors is less than optimal, to provide a desired stabilization effect. The connecting member systems can provide a rigid, semi-rigid or flexible stabilization member interconnecting two or more anchors engaged to one of more vertebral levels.

According to one aspect, a system for stabilization of a spinal column segment includes a first anchor including a distal bone engaging portion and a proximal receiver and a second anchor including a distal bone engaging portion and a proximal receiver. The connecting member includes a pair of endwalls and a pair of sidewalls extending between the endwalls along opposite sides of a longitudinal axis. The pair of endwalls and the pair of sidewalls define at least one window opening proximally and distally with the window being sized to simultaneously receive the proximal receivers of the first and second anchors. The connecting member further includes first and second mounting portions extending axially from a respective one of the endwalls and toward one another in engagement with a respective one of the proximal receivers of the first and second anchors.

In a further aspect, a connecting member links first and second anchors to one another. The connecting member includes a body extending along a longitudinal axis that defines a window opening transversely to the longitudinal axis. The window is configured with a size and shape to receive first and second anchors in the window when the first and second anchors are engaged to first and second vertebrae of a spinal column. The body further includes first and second mounting portions extending from opposite ends of the body along the longitudinal axis and into the window. The first and second mounting portions each include a terminal end in the window and the terminal ends are spaced from one another along the longitudinal axis.

In another aspect, a method for stabilizing a spinal column comprises: engaging a first anchor to a first vertebral body; engaging a second anchor to a second vertebral body; positioning a connecting member around proximal receivers of each of the first and second anchors so that the proximal receivers are positioned in a common window of the connecting member; positioning a first mounting portion extending axially into the window from a first end of the connecting member in the receiver of the first anchor and positioning a second mounting portion extending axially into the window toward the first mounting portion from an opposite end of the connecting member in the receiver of the second anchor; and securing the first and second mounting portions to the receivers of the first and second anchors.

Related features, aspects, embodiments, objects and advantages of the present invention will be apparent from the following description.

DESCRIPTION OF THE ILLUSTRATED EMBODIMENTS

Figure 1:
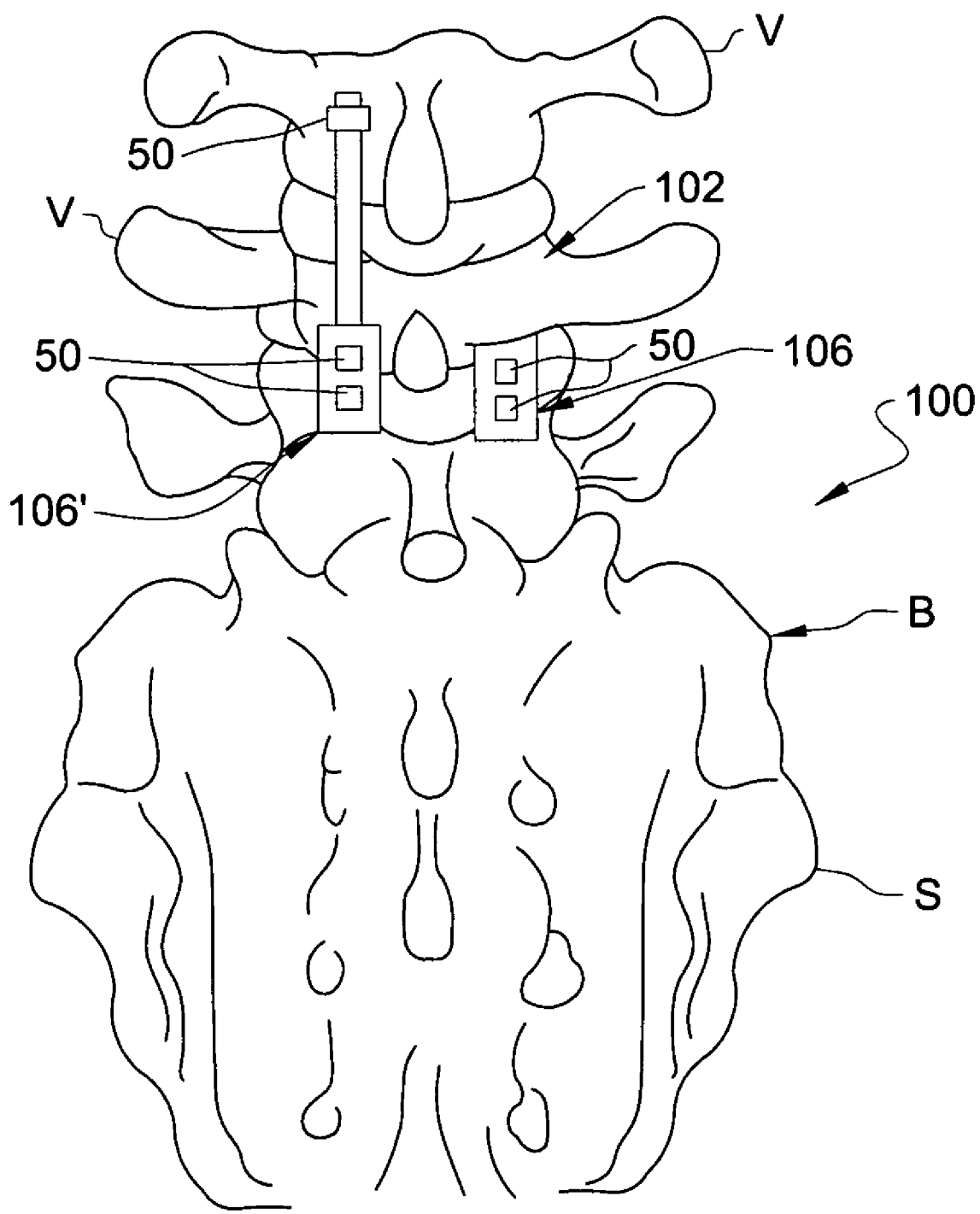
FIG. 1 is an elevation view of a spinal column segment with stabilization systems attached thereto.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Stabilization systems for stabilizing one or more vertebral levels are provided. The systems include anchors engageable to the vertebrae and a connecting member that connects the anchors to provide a stabilization effect to the vertebrae. The connecting member and/or anchors can be configured to prevent motion between the vertebrae or allow at least limited vertebral motion of the stabilized vertebral levels. The stabilization systems can be employed alone in non-fusion procedures or in conjunction interbody fusion and/or postero-lateral fusion procedures.

Systems and methods for providing dynamic or rigid stabilization of one or more spinal motion segments include a connecting member between two or more bone anchors that can be engaged to at least two or more vertebral bodies of the spinal motion segment. The connecting member includes at least one sidewall extending along a longitudinal axis and first and second mounting portions extending axially toward one another from opposite endwalls of the connecting member. The at least one sidewall and endwalls can form a common window that can receive the bone anchors therein.

The mounting portions can be in the form of rod-like projections or other suitable structure, and can be positioned in engagement with respective ones of first and second anchors. The mounting portions can be spaced from one another to facilitate flexing or other movement or displacement of the at least one sidewall to provide a flexible connecting member and dynamic stabilization effect to the vertebrae to which the anchors are engaged. Other embodiments contemplate that the at least one sidewall can include recesses or apertures to facilitate flexing of the at least one sidewall. In yet other embodiments, a third mounting portion extends from one or both of the endwalls along the axis and away from the at least one sidewall of the connecting member for engagement with an additional anchor or anchors located cephaladly and/or caudally of the vertebrae along which the at least one sidewall extends.

The anchors discussed herein can be multi-axial or uni-axial in form, and can include an anchor member engageable to a vertebral body and a receiver, post or other device for receiving or engaging a respective mounting portion of the connecting member. The multi-axial anchors allow the anchor member to be positioned at various angles relative to the receiver of the anchor. The uni-axial anchors can also provide a fixed positioning of the receiver relative to the anchor member. The anchor member of the anchors can form a distal lower portion that is engageable to a vertebral body with the proximal receiver positioned adjacent the vertebral body. In one embodiment, the anchor member is in the form of a bone screw with a threaded shaft and a proximal head that is pivotally captured in the receiver. In other embodiments, the distal anchor member can be in the form of a hook, staple, cable, tether, suture anchor, interbody fusion implant, artificial disc implant, bolt, or other structure engageable to bony tissue. The receiver can include a U-shape, O-shape, or other shape that defines a passage that receives the respective mounting portion of the connecting member therein, thereon, therethrough, or thereover, for example. The connecting member can extend from one or both of the anchors for securement to one or more additional vertebral bodies.

FIG. 1 illustrates a spinal implant system 100 located along a spinal column of a patient. More specifically, implant system 100 can be affixed to bones B of the spinal column segment 102 from a posterior approach, although application in posterior-lateral, lateral, antero-lateral and anterior approaches are also contemplated. Bones B can include the sacrum S and several vertebral bodies V. Implant system 100 generally includes several bone anchors 50 and one or more connecting members 106, 106' structured to selectively interconnect with bone anchors 50. Connecting members 106 may have a body structure with an overall length and width sized to extend between bone anchors 50 engaged to pedicles or other posterior elements of at least two vertebral bodies V. Connecting member 106' has a length sized to extend along three or more vertebrae. Connecting member 106' may extend between the other vertebrae with multiple body structures like connecting member 106 interconnected with a rod-like member. Alternatively, connecting member 106' my include a single body structure like connecting member 106 and one or more mounting portions have a rod-like configuration extending from one or both ends of the single body structure as shown.

In implant system 100, bone anchors 50 are affixed to various locations of the spinal column segment 102, such as the pedicles, and interconnected with one or more connecting members 106, 106'. Other procedures contemplate implant system 100 may be employed at other locations about the spinal column, including anterior, antero-lateral, and lateral locations. Implant system 100 may also be employed in procedures where such locations are combined; e.g. to provide posterior and anterior stabilization systems. Implant system 100 may be used for, but is not limited to, treatment of degenerative spondylolisthesis, herniation, degeneration, arthritis, fracture, dislocation, scoliosis, kyphosis, spinal tumor, and/or a failed previous fusion.

Figure 2:
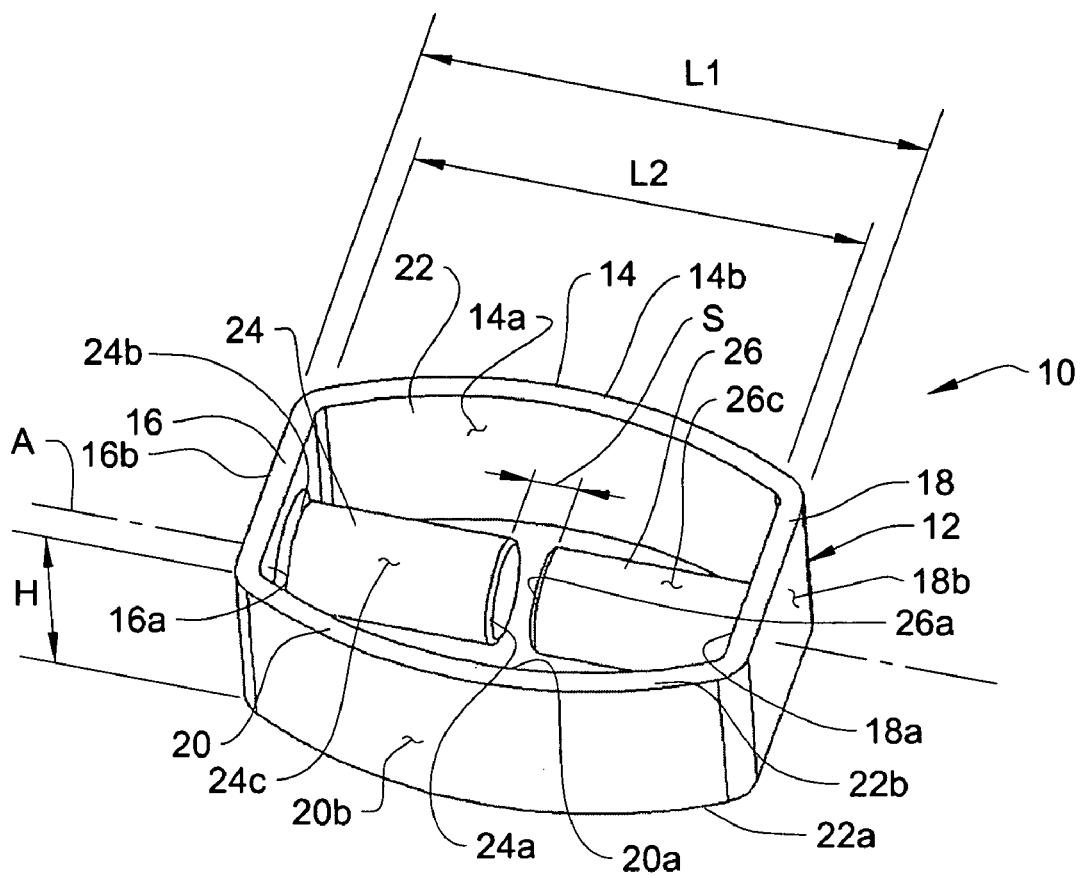
FIG. 2 is a perspective view of a connecting member comprising a portion of the stabilization system of FIG. 1.

Referring now to FIG. 2, there is shown one embodiment of connecting member 106 in the form of connecting member 10. Connecting member 10 includes a rectangular body 12 defining a window 22 extending therethrough between a distal side 22a and a proximal side 22b. Window 22 includes opposite first and second sidewalls 14, 20 extending along longitudinal axis A. Sidewalls 14, 20 are spaced laterally from longitudinal axis A. Sidewalls 14, 20 are interconnected by opposite endwalls 16, 18 that extend transversely to longitudinal axis A. First and second mounting portions 24, 26 extend from respective ones of the endwalls 16, 18 into window 22 along longitudinal axis A. Mounting portions 24, 26 include terminal ends 24a, 26a, respectively, in window 22 that are spaced from one another by gap S.

Sidewalls 14, 20 each include an inner surface 14a, 20a, respectively, extending along window 22 on opposite sides of longitudinal axis A. Sidewalls 14, 20 also include outer surfaces 14b, 20b, respectively, facing in opposite directions from one another and oriented away from longitudinal axis A. Surfaces 14a, 14b and surfaces 20a, 20b can include a form so that each of the sidewalls 14, 20 define an axially bowed shape that is concavely curved away from longitudinal axis A and away from one another. Inner surfaces 14a, 20a are concavely curved along longitudinal axis A between endwalls 16, 18, and outer surfaces 14b, 20b are convexly curved along longitudinal axis A between endwalls 16, 18 in parallel relation with the inner surfaces 14a, 20a. The bowed shape can facilitate flexing of body 12 along its length in respond to compression and tension forces applied by the spinal motion segment. Other embodiments contemplate that the sidewalls 14, 20 could be linear, inwardly concavely curved toward axis A, or include one or more offsets or other flex facilitating structure along the length thereof.

Sidewalls 14, 20 interconnect with endwalls 16, 18. Endwalls 16, 18 include inner surfaces 16a, 18a extending along window 22 and opposite outer surfaces 16b, 18b. Endwalls 16, 18 can be linear as shown, although non-linear forms are also contemplated. The outer and inner corners at the interconnections between the sidewalls and endwalls can be rounded to eliminate sharp edge and abrupt transitions where body 12 contacts tissue. Sidewalls 14, 20 and endwalls 16, 18 define a height H between distal side 22a and proximal side 22b of window 22. Furthermore, endwalls 16, 18 define a length L1 between their outer surfaces 16b, 18b and a length L2 between their respective inner surfaces 16a, 18a.

Mounting portions 24, 26 extend axially from respective ones of the inner surfaces 16a, 18a of endwalls 16, 18 into window 22. In the illustrated embodiment, mounting portions 24, 26 include a rod-like form with a circular cross-section orthogonal to longitudinal axis A. Other embodiments contemplate other forms for mounting portions 24, 26, including oval, square, rectangular, polygonal, hollow, and non-circular cross-sectional shapes. Still other embodiments contemplate the mounting portions 24, 26 include a structure to receive the receiver of the anchor, such as an eyelet, through-hole, slot, notch, clamp, or other suitable structure.

Figure 3:
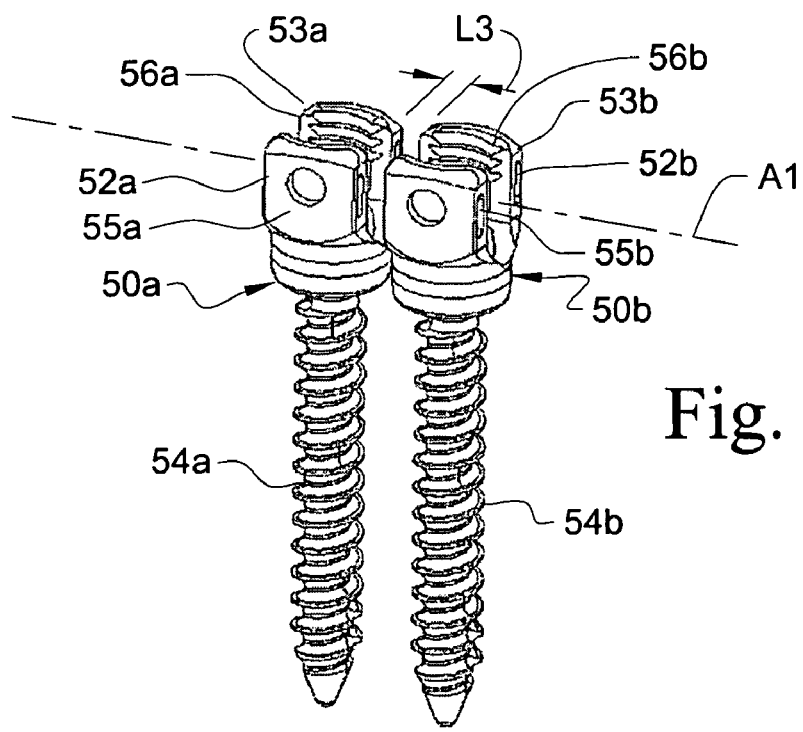
FIG. 3 is a perspective view of a pair of anchors comprising a portion of the stabilization system of FIG. 1.

Referring to FIG. 3, there is shown two anchors 50a, 50b removed from the respective vertebra for clarity but in a contemplated spatial relationship to one another. Anchors 50a, 50b each include a proximal receiver 52a, 52b and a distal bone engaging portion 54a, 54b. Bone engaging portions 54a, 54b can be in the form of a threaded, elongated shaft that threadingly engages bony structure. Other embodiments contemplate other forms for bone engaging portions 54a, 54b as discussed above. Receivers 52a, 52b can include a U-shaped saddle-like body with a pair of arms 53a, 55a and pair of arms 53b, 55b, respectively. Bone engaging portion 54a, 54b can include a proximal head (not shown) pivotally captured in a lower receptacle of the respective receiver 52a, 52b so that bone engaging portion 54a, 54b is pivotal about an axis and/or along a plane to assume any one of a plurality or infinite number of orientations relative to receiver 52a, 52b. Arms 53a, 55a and arms 53b, 55b each define a passage 56, 56b therebetween, and the passages 56a, 56b can be aligned with one another along a passage axis A1. In addition, arm pair 53a, 55a and arm pair 53b, 55b can each define a proximal opening to receive a set screw, nut, cap, plug or other engaging member (not shown) to secure connecting member 10 to the respective anchor.

When in the implanted configuration engaged to the bony structure of adjacent vertebrae, receivers 52a, 52b can be separated by a space L3. In some procedures, space L3 is sufficiently small so that a portion of a rod or other connecting element positioned in passages 56a, 56b along axis A1 is too short to provide a desired stabilization effect. Space L3 may provide insufficient length to receive, for example, a flexible portion of connecting element between receivers 52a, 52b to provide a desired dynamic stabilization effect. Space L3 can be on the order of about 2 millimeters, although other spacing distances are also contemplated.

Figure 4:
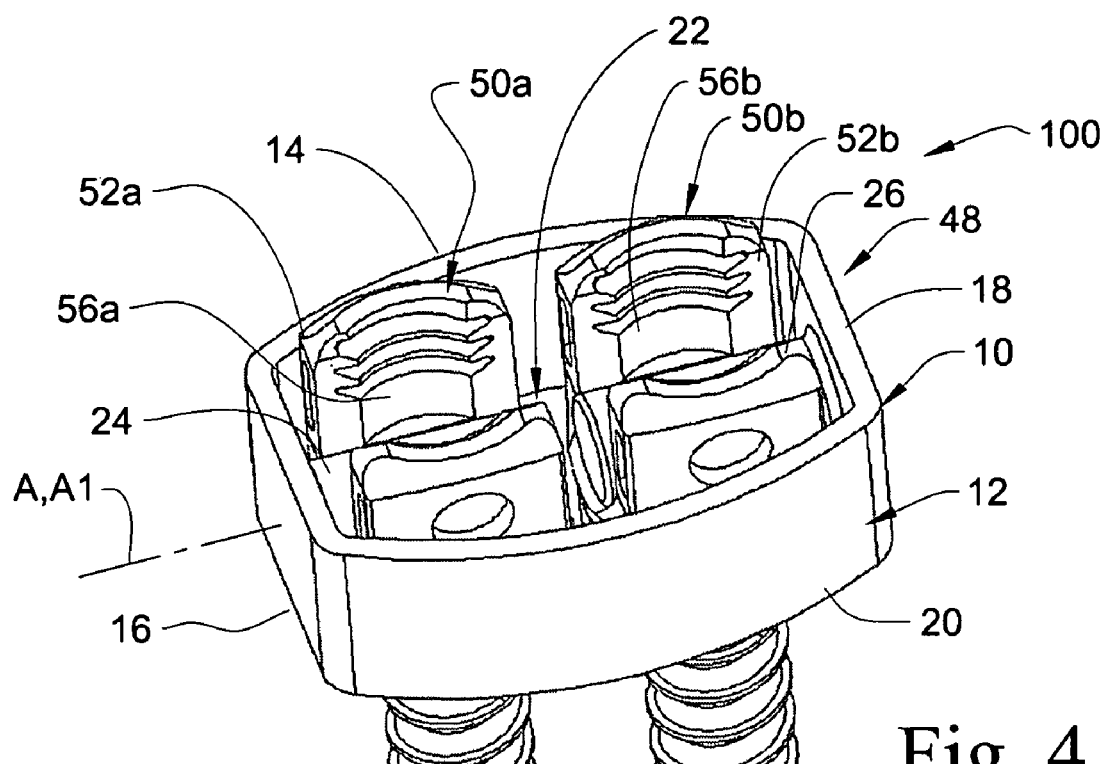
FIG. 4 is a perspective view showing the connecting member of FIG. 1 engaged to the pair of anchors of FIG. 3.

In FIG. 4 connecting member 10 is positioned for engagement with anchors 50a, 50b. Sidewalls 14, 20 are positioned on opposite sides of receivers 52a, 52b so that receivers 52a, 52b are both located in window 22. Mounting portions 24, 26 are received in passages 56a, 56b, respectively, along passage axis A1 so that passage axis A1 is aligned with longitudinal axis A. Length L2 is sized so that endwalls 16, 18 are positioned adjacent the outer sides of receivers 52a, 52b at the cephalad and caudal ends of the receivers 52a, 52b. Endwalls 16, 18 can be spaced from the respective receiver 52a, 52b, or positioned in abutting engagement therewith. The opening defined by window 22 can be sized so that the footprint of the portion of connecting member 10 projecting from or located outwardly of receivers 52a, 52b can be minimized. Height H can be sized to as to not protrude proximally from the proximal ends of receivers 52a, 52b to minimize intrusion into adjacent tissue. Embodiments where height H is sized to extend above or proximally from receivers 52a, 52b are also contemplated. Mounting portions 24, 26 are sized to be received in passages 56a, 56b of anchors 50a, 50b. Sets screws can be engaged along internal threads of the arms of receivers 52a, 52b to engage connecting member 10 to anchors 50a, 50b.

Connecting member 10 can be secured to receivers 52a, 52b to link or interconnect anchors 50a, 50b to one another. Body 12 can be made from a flexible material and/or structured to permit flexing to allow at least some motion of the spinal motion segment in response to spinal extension, flexion, lateral bending and twisting motion. Examples of suitable materials include metals and metal alloys, polymers, elastomers, ceramics, polyetheretherketone (PEEK), carbon reinforced PEEK, and other suitable biocompatible materials. In addition to material selection, flexing can be aided, as discussed above, by providing sidewalls 12, 14 with an outwardly bowed shape relative to longitudinal axis A to facilitate flexing of body 12. Other forms for sidewalls 12, 14 are also contemplated, including inwardly bowed shapes on one or both sidewalls, providing one sidewall with a bowed shape and the other with a linear shape, providing material relief along one or both sidewalls, and providing a spring or dampener interconnecting portion of one or both sidewalls.

Figure 5:
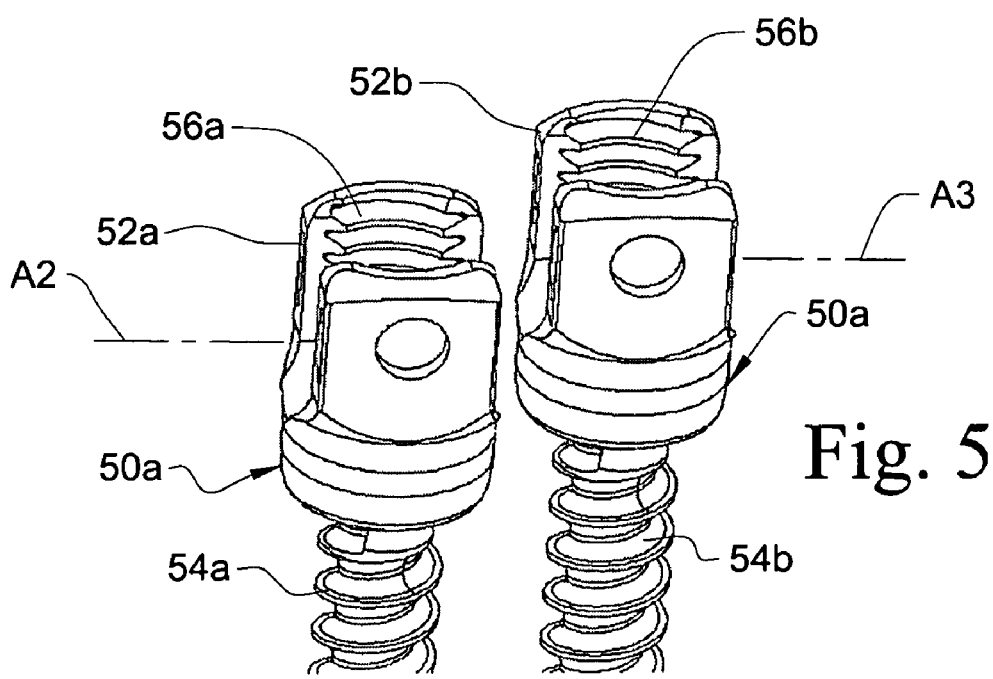
FIG. 5 is a perspective view showing the pair of anchors in an axially offset position relative to one another.
Figure 6:
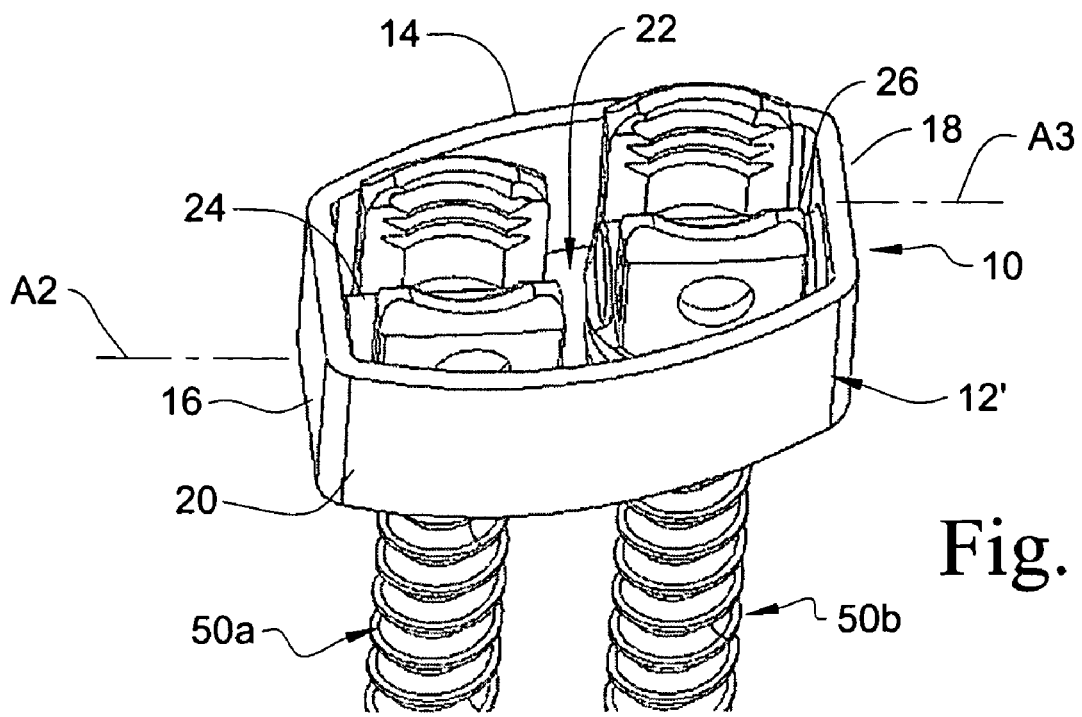
FIG. 6 is a perspective view showing the connecting member of FIG. 2 engaged to the axially offset anchors of FIG. 5.

Providing body 12 of connecting member 10 with a flexible configuration can facilitate engagement of connecting member 10 in situations where the axes of the passages of receivers 52a, 52b are not aligned with one another. For example, as shown in FIG. 5, passage 56a of receiver 52a extends along an axis A2 and passage 56b of receiver 52b extends along an axis A3. Axis A2 is offset from axis A3 so that is parallel to, oblique to or otherwise not aligned with axis A3. In addition, one or both of the axes A2 and A3 can be oriented so as to be obliquely oriented, parallel to, or otherwise not aligned with longitudinal axis A. In FIG. 6 connecting member 10 is twisted or contorted so as to be skewed relative to longitudinal axis A forming a rhombus-like shape so that body 12' is contorted to align mounting portions 24, 26 along respective ones of the axes A2, A3. Mounting portions 24, 26 can be positioned within the respective passages 56a, 56b so that anchors 50a, 50b can be linked and connected to one another even if the passages 56a, 56b are not aligned to be co-linear with one another along the same axis or along longitudinal axis A.

Figure 7:
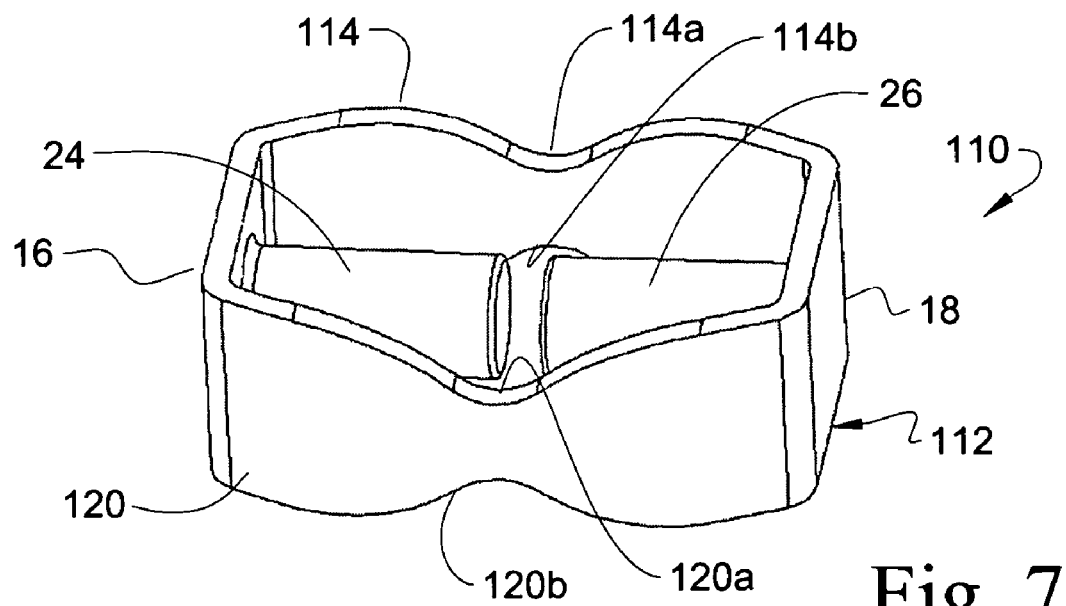
FIG. 7 is a perspective view of another embodiment connecting member.

In still other embodiments, it is contemplated that the connecting member sidewalls can be modified to facilitate flexing. For example, FIG. 7 shows a connecting member 110 that is identical to connecting member 10 except for sidewalls 114, 120. Accordingly, elements that are alike are designated with the same reference numerals. Sidewalls 114, 120 differ from sidewalls 14, 20 in that the proximal edges 114a, 120a and distal edges 114b, 120b are modified to include a concave recess at or about mid-length between endwalls 16, 18. The concave recesses can be curved as shown or in the form of one or more notches, undulations, or other relief along one or more of the proximal and/or distal edges of the sidewalls 114, 120. The recesses provide a location along the respective sidewall with reduced section modulus to facilitate bending of the respective sidewall 114, 120.

Figure 8:
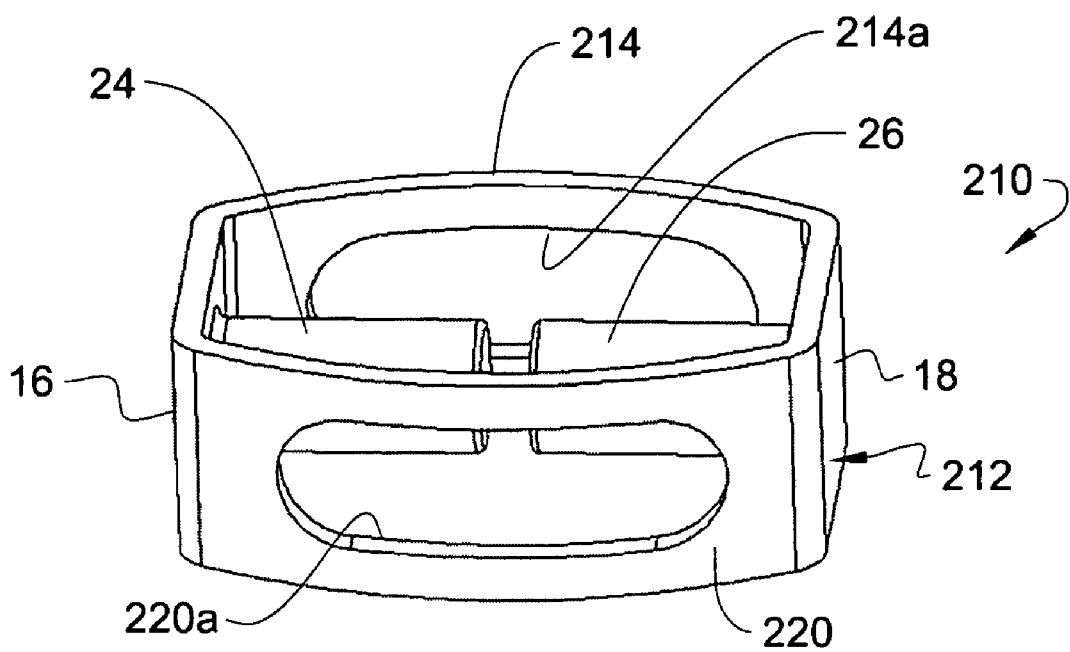
FIG. 8 is a perspective view of yet another embodiment connecting member.

In another example, FIG. 8 shows a connecting member 210 that is identical to connecting member 10 except for sidewalls 214, 220. Accordingly, elements that are alike are designated with the same reference numerals. Sidewalls 214, 220 differ from sidewalls 14, 20 in that each includes at least one aperture 214a, 220a, respectively, that extends between the inner and outer surfaces of the respective sidewall. The apertures remove material from the respective sidewall and facilitate flexing of sidewalls 214, 220 by providing a reduced section modulus to resist bending forces. Apertures 214a, 220a can be elongated along the axis of connecting member 210. Other embodiments contemplate that the sidewalls include multiple apertures, circular apertures, and/or non-circular apertures, for example.

Figure 9:
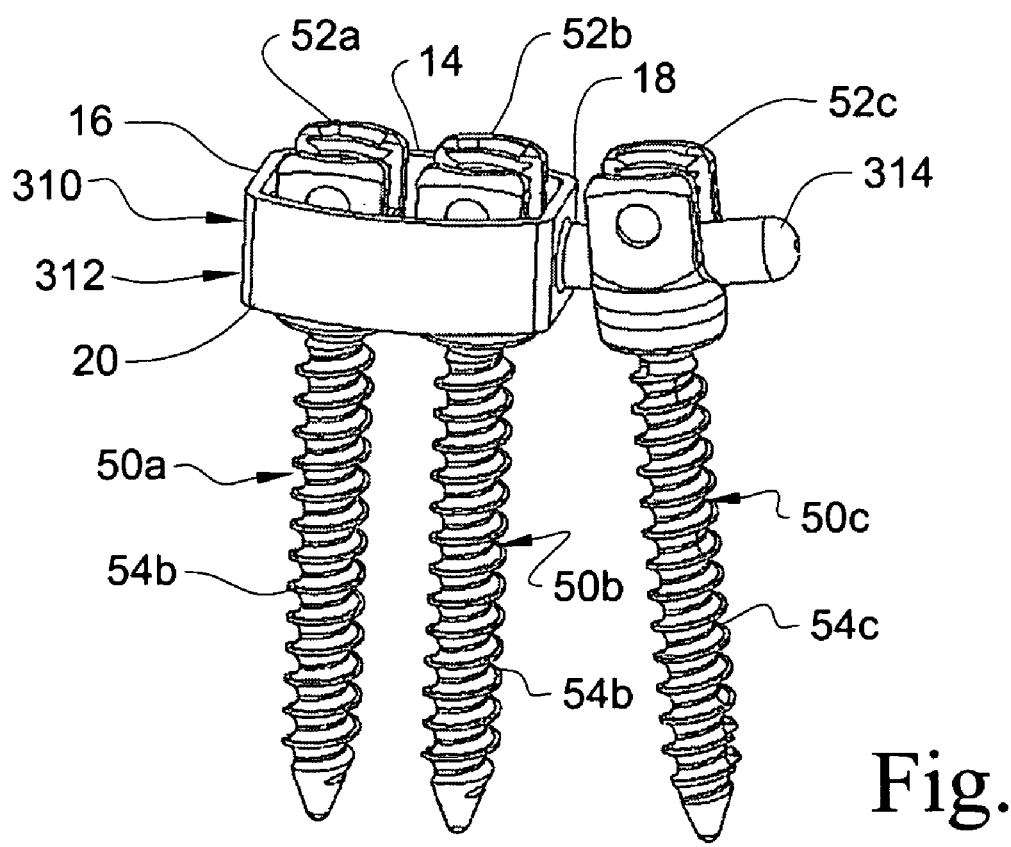
FIG. 9 is a perspective view of a multi-level stabilization system including anchors and another embodiment connecting member.

FIG. 9 shows an embodiment of connecting member 106' in the form of connecting member 310 that includes a body 312 that can be identical to connecting member 10 or any other connecting member embodiment discussed herein. Connecting member 310 can be employed in multi-level stabilization procedures. Body 312 includes a third mounting portion 314 extending axially therefrom from one of the endwalls 18 for positioning in and engagement with a receiver 52c of a third anchor 50c. Mounting portion 314 can include a rod-like body elongated and extending along the longitudinal axis of connecting member 310. Mounting portions 24, 26 and 314 can be aligned with one another and centered along the longitudinal axis, although non-aligned and/or non-centered orientations are also contemplated. In other forms, mounting portion 314 can have a length sized to extend along two or more vertebral levels for engagement with two or more anchors. The third mounting portion can extend cephaladly or caudally from body 312. In still other embodiments, a fourth mounting portion can be provided to extend axially from the other endwall 16.

Various surgical techniques can be completed with the systems discussed herein. One type of surgical technique is directed to spinal surgery for engaging at least one anchor to each of at least two vertebral bodies. The surgical technique further includes positioning a connecting member around the at least two anchors and securing mounting portions of the connecting member to respective ones of the at least two anchors. The at least two anchors can be received in a window of the connecting member that opens proximally and distally to receive receiver portions of the at least two anchors therein with the mounting portions engaged with the receivers. The connecting member may further include at least one additional mounting member extending therefrom for engagement with at least one anchor secured to at least one vertebra adjacent the vertebral level to be stabilized.

When the desired number of levels for stabilization has been selected, the anchors can be engaged to the respective vertebrae. In posterior spinal surgical techniques, the anchors can include screw or hook portions, for example, engaged in or to the pedicles of the vertebrae. The anchors can be positioned into the patient through one or more minimally invasive access portals, formed by an incision, cannula, or retractor system, for example. Placement of the anchors can be facilitated using a guidewire, image guided surgery system, fluoroscopic imaging, X-rays, CT scans, endoscopic viewing systems, microscopic viewing systems, loupes, and/or naked eye visualization, for example. With the anchors engaged to the vertebrae, the connecting member can be assembled to the anchors as discussed above.

One or more other connecting members can be similarly engaged to the spinal column along the same vertebral level or levels, or along other vertebral levels. Other procedures can also be completed in conjunction with the stabilization procedure, including discectomy, interbody fusion, artificial disc replacement, bone removal, tissue removal, intravertebral reduction, joint replacement, annular repair, and/or any other spinal surgical procedures. In multi-level stabilization procedures, one level can be fused, and the fused level and the next adjacent superior level can be stabilized with the multi-level stabilization system herein.

Although only a few exemplary embodiments of this invention have been described in detail above, those skilled in the art will readily appreciate that many modifications are possible in the exemplary embodiments without materially departing from the novel teachings and advantages of this invention. Also, features illustrated and discussed above with respect to some embodiments can be combined with features illustrated and discussed above with respect to other embodiments. Accordingly, all such modifications are intended to be included within the scope of this invention.

What is claimed is:

1. A system for stabilization of a spinal column segment, comprising:
    a first anchor including a distal bone engaging portion and a proximal receiver;
    a second anchor including a distal bone engaging portion and a proximal receiver; and
    a connecting member including a pair of endwalls and a pair of sidewalls extending between said endwalls along opposite sides of a longitudinal axis, said pair of endwalls and said pair of sidewalls define at least one window opening proximally and distally with said window being sized to simultaneously receive said proximal receivers of said first and second anchors, wherein said connecting member further includes first and second mounting portions extending axially from a respective one of said endwalls and toward one another in engagement with a respective one of said proximal receivers of said first and second anchors and each of said pair of sidewalls includes an inner surface facing said window and an opposite outer surface extending parallel to said inner surface, said inner and outer surfaces being continuously curved from one of said pair of endwalls to the other of said pair of endwalls.

2. The system of claim 1, wherein said proximal receivers each define a passage extending therethrough along said longitudinal axis and said mounting portions are positioned in a respective one of said passages.

3. The system of claim 1, wherein said proximal receivers each define a passage extending therethrough along a respective one of first and second axes that are not aligned with said longitudinal axis, and further wherein said connecting member is flexed to orient each of said mounting portions in alignment with a respective one of said first and second axes.

4. The system of claim 3, wherein said mounting portions each include a rod-like body extending on said longitudinal axis when said connecting member is not flexed.

5. The system of claim 4, wherein said mounting portions each extend from said respective endwall to a terminal end of said respective mounting portion located in said window, said terminal ends separated from one another by a gap.

6. The system of claim 1, wherein said inner surfaces each define a concave curvature away from said longitudinal axis and between said pair of endwalls.

7. The system of claim 6, wherein said sidewalls each include a proximal edge and a distal edge extending thereaolong between said endwalls, at least one of said proximal and distal edges of each of said sidewalls including a concave recess.

8. The system of claim 6, wherein said sidewalls each include at least one aperture extending therethrough from said inner surface to said outer surface of said respective sidewall.

9. The system of claim 6, wherein said endwalls are linear between said pair of sidewalls.

10. The system of claim 1, further comprising a third mounting portion extending along said longitudinal axis from one of said pair of endwalls in a direction opposite the other of said pair of endwalls.

11. The system of claim 10, wherein said first, second and third mounting portions each include a rod-like body with a circular cross-section extending from said respective endwall to a terminal end of said respective mounting portion.

12. The system of claim 11, wherein said first, second and third mounting portions are all aligned along said longitudinal axis.

13. A connecting member for linking first and second anchors to one another, comprising:
    a body extending along a longitudinal axis, wherein said body includes a pair of sidewalls spaced from one another on opposite sides of said longitudinal axis and extending along said longitudinal axis, said body further including a pair of endwalls at opposite ends of said sidewalls, said endwalls extending between and interconnecting said sidewalls, said pair of endwalls and said pair of sidewalls of said body defining a rhombus shape extending around a window opening transversely to said longitudinal axis, said window being configured with a size and shape to receive first and second anchors in said window when the first and second anchors are engaged to first and second vertebrae of a spinal column, said body further including first and second mounting portions extending from opposite ends of said body along said longitudinal axis into said window, said first and second mounting portions each including a terminal end in said window and said terminal ends are spaced from one another along said longitudinal axis.

14. The connecting member of claim 13, wherein said first and second mounting portions each include a first end engaged with a respective one of said pair of endwalls and said respective terminal end is opposite said respective first end.

15. The connecting member of claim 14, wherein said body further includes a third mounting portion extending from one of said endwalls of said body, said third mounting portion being generally aligned with said first and second mounting portions along said longitudinal axis.

16. The connecting member of claim 13, wherein said body is flexible to re-orient said mounting portions relative to said longitudinal axis.

17. The connecting member of claim 13, wherein said sidewalls each include an inner surface along said window and an opposite outer surface, said inner surfaces each being concavely curved away from said longitudinal axis between said endwalls and said outer surfaces each being convexly curved along said longitudinal axis between said endwalls.

18. A method for stabilizing a spinal column, comprising:
engaging a first anchor to a first vertebral body;
engaging a second anchor to a second vertebral body;
positioning a connecting member around proximal receivers of each of the first and second anchors so that the proximal receivers are positioned in a common window of the connecting member;
positioning a first mounting portion extending from a first end of the connecting member in engagement with the receiver of the first anchor; and
positioning a second mounting portion extending from a second end of the connecting member opposite the first end in engagement with the receiver of the second anchor, wherein during positioning the first mounting portion and the second mounting portion the connecting member is contorted so that the connecting member is skewed relative to the longitudinal axis to form a rhombus-like shape.

19. The method of claim 18, wherein the connecting member includes first and second sidewalls extending along opposite sides of a longitudinal axis and first and second endwalls at respective ends of the first and second sidewalls extending between the first and second sidewalls, the window being defined by the first and second sidewalls and the first and second endwalls.

20. The method of claim 19, wherein the first and second mounting portions are aligned along the longitudinal axis and the receivers each define a passage aligned along the longitudinal axis for receiving the respective mounting portion therein.

21. The method of claim 20, wherein the first and second mounting portions extend from a respective one of the first and second endwalls to a terminal end of the respective mounting portion located in the window, the terminal ends being spaced from one another in the window along the longitudinal axis.

22. The method of claim 19, wherein the first and second mounting portions are aligned along the longitudinal axis and the receivers each define a passage extending along an axis that is not aligned with the longitudinal axis, and further comprising flexing the connecting member to align the first and second mounting portions with the passage of the respective receiver of the first and second anchors.

23. The method of claim 19, further comprising flexing the first and second sidewalls in response to movement of the first and second anchors toward one another and in response to movement of the first and second anchors away from one another.

24. The method of claim 18, further comprising engaging a third anchor to a third vertebra and securing a third mounting portion of the connecting member to the third anchor wherein the third mounting portion extends from the second end of the connecting member in a direction opposite the second mounting portion.

25. The method of claim 24, wherein:
the connecting member includes first and second sidewalls extending along opposite sides of a longitudinal axis and first and second endwalls at respective ends of the first and second sidewalls extending between the first and second sidewalls, the window being defined by the first and second sidewalls and the first and second endwalls;
the first and second mounting portions extend along the longitudinal axis into the window from respective ones of first and second endwalls to a terminal end of the respective mounting portion, the terminal ends being spaced from one another in the window; and
the third mounting portion extends from one of the first and second endwalls along the longitudinal axis in a direction away from the window.

26. The method of claim 25, wherein the first, second and third mounting portions each include a rod-like body and are aligned with one another along the longitudinal axis.

* * * * *